United States Patent [19]

Blacklock et al.

[11] Patent Number: 5,688,968
[45] Date of Patent: Nov. 18, 1997

[54] ENANTIOSELECTIVE SYNTHESIS OF 5,6-DIHYDRO-(S)-4-(ETHYLAMINO)-(S)-6-METHYL-4H-THIENO[2,3-B]THIOPYRAN-2-SULFONAMIDE 7,7-DIOXIDE

[75] Inventors: Thomas J. Blacklock, Clark; David J. Mathre, Skillman; Paul Sohar, Warren, all of N.J.

[73] Assignee: Merck & Co., Inc., Rahway, N.J.

[21] Appl. No.: 369,557

[22] Filed: Jan. 6, 1995

Related U.S. Application Data

[63] Continuation of Ser. No. 195,886, Feb. 10, 1994, abandoned, which is a continuation-in-part of Ser. No. 35,523, Mar. 23, 1993, abandoned.

[51] Int. Cl.$^6$ .................................. C07D 495/04
[52] U.S. Cl. .................................. 549/23; 547/66
[58] Field of Search .................................. 549/23.66

[56] References Cited

U.S. PATENT DOCUMENTS

| | | | |
|---|---|---|---|
| 4,797,413 | 1/1989 | Baldwin et al. | 514/432 |
| 4,968,814 | 11/1990 | Blacklock et al. | 549/66 |
| 5,091,409 | 2/1992 | Baldwin et al. | 514/434 |

OTHER PUBLICATIONS

Brown, et al., Journal of Organic Chemistry, Selective Reductions. XVII. The Fast Reaction of Primary, Secondary, and Tertiary Amides with . . . vol. 38, No. 5, pp. 912–916, (1973).

Popova, et al., Chemical Abstracts, vol. 113, No. 25, AB No. 231685v, p. 752, (1990).

Wann, et al., Journal of Organic Chemistry, Reduction of Carboxylic Acid Derivatives by BH4–in Acidic Dimethyl Sulfoxide, vol. 46, No. 12, pp. 2579–2581, (1981).

J. March, Advanced Organic Chemistry, pp. 879–880 (2d Ed., McGraw–Hill).

J. March, Advanced Org. Chem.; pp. 879–880 (2d Ed., McGraw–Hill). (1990).

Brown, et al., *J. Org. Chem.*, Selective Reductions, XVIII. The Fast Reaction of Primary, Secondary, and Tertiary Amides with . . . ; vol. 38, No. 5, pp. 912–916, (1973).

Popova, et al., *Chem. Abst.;* vol. 113, No. 25, AB No. 231686v, p. 752, (1990).

Wann, et al., *J. Org. Chem.*, Reduction of Carboxylic Acid Derivatives by BH –4–in Acidic Dimethyl Sulfoxide; vol. 46, No. 12, pp. 2579–2581 (1981).

Jones et al, "An Asymmetric Synthesis of MK–0417. Observations on . . . " J. Org. Chem, 1991, 56, 763–769.

Blacklock et al "An Enantioselective Synthesis of the Toprally–Active Carboniz . . . " J. Org. Chem. 1993, 58, 1672–1679.

March, "Adv. Org. Chem.," 3rd Ed, 1990, pp. 860–861.

Carey et al. "Adv. Org. Chem. Part B: Reactions & Synthesis," 3rd Ed., Plenum Press, NY, 1990 p. 238.

*Primary Examiner*—Shailendra Kumar
*Assistant Examiner*—Mary C. Cebulak
*Attorney, Agent, or Firm*—Sylvia A. Ayler; Mark R. Daniel

[57] ABSTRACT

A key step in the synthesis of 5,6-dihydro-(S)-4-(ethylamino)-(S)-6-methyl-4H-thieno[2,3-b]thiopyran-2-sulfonamide 7,7-dioxide (dorzolamide) and related compounds is a Ritter reaction with an unexpected tendency to proceed with retention of chirality.

8 Claims, No Drawings

ENANTIOSELECTIVE SYNTHESIS OF 5,6-DIHYDRO-(S)-4-(ETHYLAMINO)-(S)-6-METHYL-4H-THIENO[2,3-B]THIOPYRAN-2-SULFONAMIDE 7,7-DIOXIDE

This is a continuation of application Ser. No. 08/195,886 filed on Feb. 10, 1994, now abandoned, which is a continuation in-part of application U.S. application Ser. No. 08/035,523, filed Mar. 23, 1993 now abandoned.

BACKGROUND OF THE INVENTION

The current therapy for control of elevated intraocular pressure (IOP) or ocular hypertension which is believed to be a factor in the onset and progress of glaucoma is typically effected with a variety of topically applied agents which fall within four categories: β-blockers, sympathomimetic agents, parasympathomimetic agents and cholinesterase inhibitors. The adjuvant oral administration of a carbonic anhydrase inhibitor (CAI) is practised when the above-described topical agent's side effects limits its use and/or it fails to achieve adequate IOP control. The orally active CAI's can exhibit serious side-effects such as anorexia, gastrointestinal upset and parasthesias. Therefore an intense and ongoing search has been mounted for a topically active CAI that would not exhibit such side effects due to the route of administration and inherent target organ specificity. This search has resulted in the discovery of a class of compounds by Baldwin et al (U.S. Pat. No. 4,797,413) of general formula:

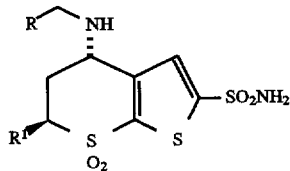

wherein R and $R^1$ are lower alkyl, especially dorzolamide, wherein R is ethyl and $R^1$ is methyl.

The Ritter reaction is well-known in the art and consists of the treatment of an aliphatic hydroxyl with a nitrile and a strong acid to form an amide.

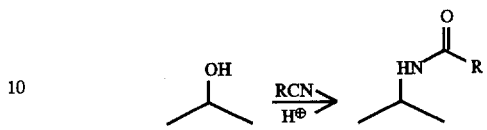

The reaction proceeds through a carbonium ion at the point of attachment of the —OH so that if that is a chiral center in the starting material the chirality is lost during the reaction and a racemic product results.

With the present invention the Ritter reaction is employed to introduce the nitrogen function at the 4-position of the molecule starting with a pure enantiomer and the chirality is unexpectedly retained in the product.

SUMMARY OF THE INVENTION

This invention is concerned with a process for the synthesis of the dorzolamide type of compound in high yield and high enantiomeric purity. The key step in this novel process is a Ritter reaction with an unexpected and unprecedented tendency to proceed with retention of chirality.

DETAILED DESCRIPTION OF THE INVENTION

The novel process of the present invention can be depicted as shown in Scheme I:

SCHEME 1

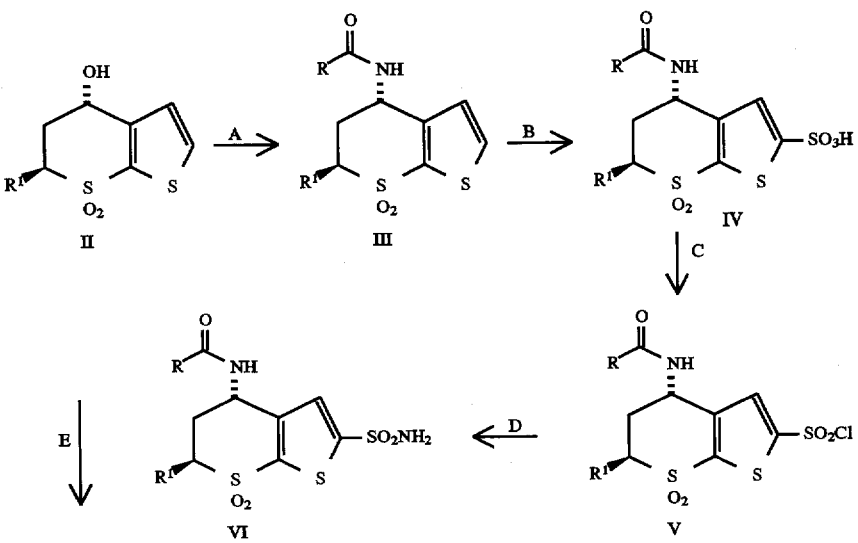

-continued
SCHEME 1

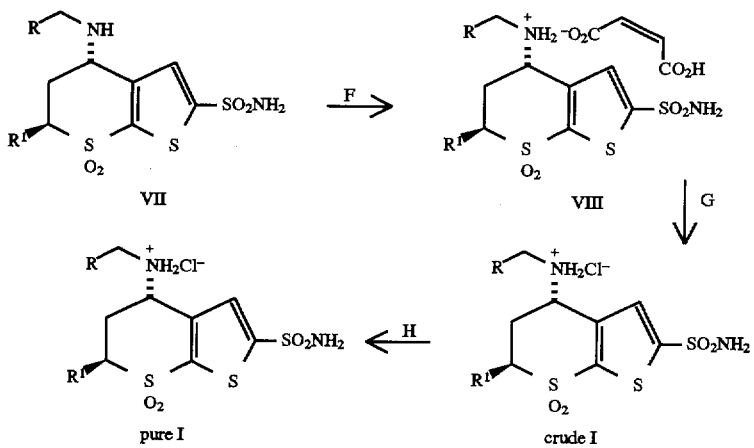

wherein R and $R^1$ are the same or different and are $C_{1-3}$ alkyl.

Step A of Scheme I is a Ritter reaction or modification thereof comprising the slow addition of about a 10–15 fold molar excess of a strong acid such as concentrated sulfuric acid or a mixture of concentrated sulfuric acid and fuming sulfuric acid to a stirred cold solution of II in a nitrile of structure RCN wherein R is $C_{1-3}$ alkyl such as methyl, ethyl, propyl or isopropyl. The mount of water present during the Ritter reaction is critical for optimum preservation of chirality and it varies (0.5–10%) according to the acid employed. Commercial sulfuric acid can introduce too much water into the system and the water is reduced by the addition of fuming sulfuric acid. However, anhydrous acids such as methanesulfonic, trifluoroacetic acid or borotrifluoride etherate require the addition of water to the reaction. Temperatures of about −20° C. to about 0° C. are satisfactory, especially about −5° C. After addition of the acid the mixture is allowed to warm spontaneously while stirring until the reaction is complete, in about 12 to 18 hours. The reaction is quenched by adding the mixture to water, the acid is neutralized by the addition of base such as sodium hydroxide, and the product is extracted with an organic solvent such as ethyl acetate.

Step B comprises sulfonylation of III by adding it to cooled chlorosulfonic acid or filming sulfuric acid at about 0° C. at such a rate to maintain the temperature below about 20° C. The resulting mixture is then heated at about 40°–60° C. until the reaction is complete in about 10 to 15 hours. This material is used directly in the next step.

Step C, the chlorination, comprises the slow addition of thionyl chloride to the cooled (15°–25° C.) solution of IV followed by heating at about 40°–60° C. for about 4 to 8 hours.

The reaction is quenched by slow addition of the mixture to stirred, cooled water followed by collection of the product by filtration.

Step D, or the amidation procedure, to form sulfonamide V comprises the slow addition of V to a cooled (−15°–0° C.) solution of aqueous ammonia in THF at a rate to maintain the temperature below about 0° C. followed by stirring at about 0° C. for about 0.5 to 2 hours. The product is isolated by adjusting to pH 3–5 with conc. sulfuric acid, separating the organic layers, diluting with water and concentrating which causes crystallization.

Step E comprises reduction of the amide carbonyl of compound VI by slowly adding a Lewis acid such as boron trifluoride etherate or aluminum chloride or an anhydrous strong acid such as methanesulfonic acid or trifluoroacetic acid to a stirred slurry of VI and sodium borohydride in dry THF at about −5° C. to about +5° C. followed by stirring about 4 to 6 hours at about −5° to +5° C. followed by 12 to 18 hours at about 25°–40° C. On completion, the reaction mixture is slowly added to cooled dilute acid followed by isolation by standard procedures if desired. As one skilled in the art would appreciate, the above reaction with sodium borohydride in dry THF and an acid such as boron trifluoride etherate or methanesulfonic acid produces borane-tetrahydrofuran in the process of forming compound VII. Alternatively, compound VII can be formed by reducing compound VI with borane-tetrahydrofuran or borane-dimethyl sulfide, without use of the acid.

The maleate salt VIII is formed by standard procedures, converted to the crude hydrochloride salt I and recrystallized to form pure I.

These reaction steps are exemplified by the Example that follows.

The product of the novel process of this invention is a topically effective carbonic anhydrase inhibitor useful in the treatment of ocular hypertension. It is administered topically to the eye usually as a solution, comprising about 0.1% to 15% by weight of compound, one or two drops at a time, one to four times a day.

EXAMPLE 1

Step A: Sulfuric Acid Ritter Procedure

To a mechanically stirred, cooled (−5°±5° C.) solution of hydroxysulfone II (25.0 g, 0.114 mol; 98:2 trans/cis) in acetonitrile (300 mL) was slowly added concentrated sulfuric acid (18M, 86 mL, 1.52 mol) over a 0.5 h period while maintaining the internal temperature at −5°±5° C. The mixture was allowed to warm to 20°±5° C. and was stirred at this temperature for 12–18 h, or until the reaction was judged to be complete by HPLC.

| | |
|---|---|
| Assay Procedure: | An aliquot (0.1 mL) was diluted to 50.0 mL with $H_2O$ and then analyzed by the following HPLC method. |
| Instrument: | Spectra Physics 8800 |
| Column: | 4.1 × 250 mm Ultrasphere C-8 (Altex Inc.) |
| Eluent A: | $H_2O$ (0.1% v/v $H_3PO_4$) |

| | | |
|---|---|---|
| Eluent B: | MeCN | |
| Isocratic: | 87:13 A:B for 7 min; then | |
| Gradient: | 87:13 to 35:65 A:B over 14 min | |
| Flow Rate: | 2.0 mL/min | |
| Temperature: | 45° C. | |
| Injection: | 10.0 μL | |
| Detection: | UV (230 nm) | |
| Retention Times: | Hydroxysulfone II (cis isomer) | 6.0 min |
| | Hydroxysulfone II (trans isomer) | 6.6 min |
| | Acetamidosulfone III (cis isomer) | 7.6 min |
| | Acetamidosulfone III (trans isomer) | 8.5 min |

The reaction was considered complete when less than 1% of hydroxysulfone II (vs. the acetamidosulfone III product) remained. At the end of the reaction the trans/cis ratio of the acetamidosulfone III product was 92.4:7.6.

After the reaction was complete, the reaction mixture was slowly added to a mechanically stirred, pre-cooled (0°–5° C.) quench mixture of ethyl acetate (1.7 L) and water (800 mL). At the same time, 50% (w/w) aqueous sodium hydroxide (185 mL) was added to the quench mixture at such a rate that the pH was maintained between 3–5 and the internal temperature was maintained below 25° C. The pH was then further adjusted to 7.0–7.5 with additional sodium hydroxide, and the mixture stirred for 1 h at 30° C. The mixture was filtered to remove the sodium sulfate, and the filter cake washed with ethyl acetate (300 mL). The filtrate and cake washes were combined, and the mixture partitioned. The aqueous (lower) phase was extracted once with ethyl acetate. The organic (upper) phases were combined and then concentrated in vacuo (10 mBar, 50° C.) to a volume of 100 mL. Hexane (300 mL) was added slowly, and the mixture stirred for 1 h at 20°–22° C. The mixture was filtered, and the product cake washed with hexane (1 bed volume). The product was air-dried, then dried in vacuo (100 mBar, nitrogen sweep, 30°–35° C.) to constant weight.

Yield: 31.0 g (95% based on HPLC wt % purity) of crude acetamidosulfone III as a white solid. The crude product also contains a small amount of acetamide and sodium acetate. $^1$H NMR: (DMSO-$d_6$) δ8.57 (br d, 1H, J=8.5 Hz), 8.53 (br d, 1H, J=11.7 Hz), 7.96 (d, 1H, J=5.0 Hz), 7.94 (d, 1H, J=5.0 Hz), 7.03 (d, 1H, J=5.0 Hz), 6.95 (d, 1H, J=5.0 Hz), 5.21–5.14 (m, 2H), 3.84–3.76 (m, 2H), 2.51–2.36 (m, 2H), 2.29–2.2 (m, 2H), 1.84 (s, 3H), 1.75 (s, 3H), 1.35 (d, 3H, J=6.8 Hz), 1.32 (d, 3H, J=6.2 Hz). HPLC: 93:7 trans/cis (above method). Microanalysis: Anal. Calcd for $C_{10}H_{13}NO_3S_2$: C, 46.32; H, 5.05; N, 5.40; S, 24.73. Found: C, 46.41; H, 4.94; N, 5.34; S, 24.55.

Step A (Alternate): Sulfuric Acid/Fuming Sulfuric Acid Ritter Procedure

To a mechanically stirred, cooled (−5°±5° C.) solution of hydroxysulfone II (10.0 g, 45.8 mmol; 98:2 trans/cis) in acetonitrile (50 mL) was slowly added concentrated sulfuric acid (18M, 9.0 mL, 162 mol) while maintaining the internal temperature at <10° C., followed by 30% fuming sulfuric acid (1.2 mL). The mixture stirred for 2 h at 15°–20° C., then 3 h at 20°–22° C. [At temperature above 25° C. significant amounts of acetamide are formed.] The progress of the reaction was monitored by HPLC (method described in example 1). The reaction was considered complete when less than 1% of hydroxysulfone II (vs. the acetamidosulfone III product) remained. At the end of the reaction the trans/cis ratio of the acetamidosulfone III product was 93.5:6.5. After the reaction was complete, the mixture was poured into ice (100 g), and the pH of the mixture adjusted to 3.5–5.5 by the slow addition of 50% aqueous sodium hydroxide (ca. 20 mL). The mixture was extracted with ethyl acetate (2×100 mL). The ethyl acetate extracts were combined and washed with brine (1×50 mL). The solution was then concentrated in vacuo (100 mBar, 35°–40° C.) to a volume of 20 mL. Ethyl acetate (100 mL) was added and the concentration repeated (final volume 20 mL) to insure complete removal of acetonitrile. Hexane (100 mL) was added slowly, and the mixture stirred for 2 h at 20°–22° C. The mixture was filtered, and the product cake washed with hexane (1 bed volume). The product was air-dried, then dried in vacuo (100 mBar, nitrogen sweep, 30°–35° C.) to constant weight.

Yield: 11.5 g (97%) of crude acetamidosulfone III as a white solid. In this case the crude product is free of acetamide and sodium acetate. $^1$H NMR: consistent. HPLC: 93.5:6.5 trans/cis (above method).

Step B: Sulfonylation Procedure

To mechanically stirred, cooled (0° C.) chlorosulfonic acid (70 mL, 1.05 mol) was added the crude acetamidosulfonamide III (29.7 g, 0.114 mol; 93:7 trans/cis) portionwise at a rate to maintain the internal temperature <20° C. The dark sulfonylation reaction mixture was heated to 50° C. for 12 h, or until the reaction was judged to be complete by HPLC. [Note: during the reaction hydrogen chloride (0.114 mol) was evolved.]

Assay Procedure: An aliquot (0.1 mL) is diluted to 100.0 mL with $H_2O$ and then analyzed by the following HPLC method. Instrument: Spectra Physics 8800. Column: 4.1× 250 mm Ultrasphere C-8 (Altex Inc.). Eluent A: $H_2O$ (0.1% v/v $H_3PO_4$). Eluent B: MeCN. Gradient: 97:3 to 35:65 A:B over 25 min. Flow Rate: 2.0 mL/min. Temperature: 45° C. Injection: 10.0 μL. Detection: UV (230 nm). Retention Times: Sulfonic Acid IV (cis/trans isomers) 5.0 min, Acetamidosulfone III (cis isomer) 9.0 min, Acetamidosulfone III (trans isomer) 10.0 min.

The sulfonylation reaction was considered to be complete when less than 1% of acetamidosulfone III (vs. the sulfonic acid IV product) remained.

Step C: Chlorosulfonylation Procedure

After the Step B reaction was complete, the mixture was cooled to 20° C. Thionyl chloride (70 mL, 0.96 mol) was then slowly added at a rate to control the evolution of hydrogen chloride (0.114 mol) and sulfur dioxide (0.114 mol). Following the addition, the mixture was heated to 50° C. for 6 h, or until the reaction was judged to be complete by HPLC.

Assay Procedure: An aliquot (0.1 mL) is diluted to 50.0 mL with acetonitrile and then immediately analyzed by the above HPLC method (to minimize hydrolysis of the sufonyl chloride V product). Retention Times: Sulfonic Acid IV (cis/trans isomers) 5.0 min, Sulfonyl Chloride V (cis/trans isomers) 19 min.

The reaction was considered to be complete when less than 1% of the sulfonic acid IV (vs. the sulfonyl chloride V product) remained. After the reaction was complete, the mixture was cooled to 15°–20° C., and then metered slowly into vigorously stirred water (1.4 L), pre-cooled to 0°–5° C., at a rate to maintain the temperature <5° C. [Note: the internal temperature must not be allowed to rise above 5° C. to minimize hydrolysis of the sulfonyl chloride V product.] After the addition of ca. 10% of the reaction mixture, the quench mixture can be further cooled to −5°±5° C. During the quench, significant amounts of hydrochloric acid and sulfurous acid are generated. The mixture was stirred for 1 h at 0°–5° C., was filtered, and the product cake then washed with cold (5° C.) water (1 L). The cake was sucked well to remove as much water as possible.

Yield: 68 g of crude sulfonyl chloride V as a moist solid (ca. 40 wt % water), which was used immediately in the next step. $^1$H NMR: (CDCl$_3$) δ7.74 (s, 1H), 8.07 (br d, 1H, J=8.1 Hz), 5.45–5.35 (m, 1H), 3.63–3.56 (m, 1H), 2.64–2.56 (m, 2H), 2.09 (s, 3H), 1.57 (d, 1H, J=6.9 Hz).

Step D: Amidation Procedure

To a mechanically stirred, cooled (–10°±5° C.) solution of concentrated aqueous ammonia (15M, 43 mL, 0.65 mol) in tetrahydrofuran (THF, 300 mL) was added the crude sulfonyl chloride V (68 g wet, ca. 40.9 g, 0.114 mol) portionwise at a rate that maintained the internal temperature below 0° C. After the addition was complete, the mixture was stirred at 0°–5° C. for 1 h, or until the reaction was judged to be complete by HPLC.

Assay Procedure: An aliquot (0.1 mL) is diluted to 50.0 mL with acetonitrile and then immediately analyzed by the HPLC method described in example 3 (to minimize hydrolysis of the sufonyl chloride V starting material). Retention Times: Acetamidosulfonamide VI (cis isomer) 9.0 min, Acetamidosulfonamide VI (trans isomer) 10.0 min, Sulfonyl Chloride V (cis/trans isomers) 19 min.

The reaction was considered complete when less than 1% of sulfonyl chloride V (vs. the acetamidosulfonamide VI product) remained. After the reaction was complete, the pH of the mixture was adjusted to 3–5 by the dropwise addition of concentrated sulfuric acid (18M, ca. 12.2 mL, 0.218 mol) while maintaining the internal temperature below 20° C. The mixture was allowed to settle, and the layers separated. The aqueous (lower) phase was extracted with THF (70 mL). The two organic layers were combined and then diluted with water (250 mL). The solution was then concentrated by distillation to a volume of 125 mL. During the concentration the product spontaneously crystallized. The slurry was diluted with water to a volume of 250 mL and the mixture then stirred for 12–18 h at 20°–25° C. The mixture was filtered, and the product cake washed with water (150 mL). The product was air-dried, then dried in vacuo (100 mBar, nitrogen sweep, 55° C.) to constant weight.

Yield: 29.5 g (76% yield from hydroxysulfone II) of acetamidosulfonamide VI as a white crystalline solid. HPLC: 95:5 trans/cis (above method). $^1$H NMR: (DMSO-d$_6$) δ8.65 (br d, 1H, J=9.5 Hz), 8.60 (br d, 1H, J=9.5 Hz), 8.05 (br s, 4H), 7.42 (s, 1H), 7.31 (s, 1H), 5.32–5.15 (m, 2H), 4.10–3.80 (m, 2H), 2.53–2.41 (m, 2H), 2.34–2.18 (m, 2H), 1.91 (s, 3H), 1.87 (s, 3H), 1.37 (d, 3H, J=7.0 Hz), 1.34 (d, 3H, J=7.6 Hz). Microanalysis: Anal. Calcd for C$_{10}$H$_{14}$O$_5$N$_2$S$_3$: C, 35.49; H, 4.17; N, 8.28; S, 28.42. Found: C, 35.60; H, 4.04; N, 8.21; S, 28.40.

Step E: Reduction via Borane Generated in situ Procedure

To a mechanically stirred, cooled (0°–5° C.) slurry of acetamidosulfonamide VI (29.5 g, 87.1 mmol; 95:5 trans/cis) and sodium borohydride (16.9 g, 447 mmol) in dry THF (290 mL) was added neat boron trifluoride etherate (8.13M, 73 mL, 593 mmol) over a 0.5 h period while maintaining the internal temperature below 5° C. [Caution: hydrogen is generated during the reaction as sodium borohydride and/or diborane reacts with the sulfonamide protons.] After the addition was complete the mixture was stirred for 5 h at 0°–5° C. and then at 30°–35° C. for 12–18 h, or until the reaction was judged to be complete by HPLC.

Assay Procedure: An aliquot (0.1 mL) is diluted to 50.0 mL with H$_2$O and then analyzed by the HPLC method described in example 3. Retention Times: Aminosulfonamide VII (cis isomer) 4.5 min, Aminosulfonamide VII (trans isomer) 5.0 min, Acetamidosulfonamide VI (cis isomer) 9.0 min, Acetamidosulfonamide VI (trans isomer) 10.0 min, Amine-borane complex 14–20 min.

The reaction was considered to be complete when less than 1% of acetamidosulfonamide VI (vs. the aminosulfonamide VII product) remained. After the reaction was complete, the reaction mixture was slowly added to a mechanically stirred, pre-cooled (0°–5° C.) solution of 1M aqueous sulfuric acid (400 mL) at such a rate that the internal temperature was maintained below 20° C. [Caution: hydrogen is generated during the quench.] The mixture was stirred for 2 h at 20°–25° C., or until the generation of hydrogen ceased. The mixture was then concentrated by distillation (1 atm) to a volume of 400 mL. The resultant aqueous solution was cooled to 10° C. and the pH cautiously adjusted to 4–5 by the dropwise addition of 50% aqueous sodium hydroxide (ca. 37 mL, 0.7 mol) while the internal temperature was maintained below 20° C. Ethyl acetate (600 mL) was added and the pH further adjusted to 7.5–8.0 by the addition of saturated aqueous sodium bicarbonate (ca. 75 mL, 90 mmol). The mixture was filtered to remove the sodium sulfate generated during the initial pH adjustment, and the filter cake washed with ethyl acetate (100 mL). The filtrate and cake wash were combined and the resultant mixture partitioned. The aqueous (lower) phase was extracted with ethyl acetate (100 mL). The organic layers were combined and then washed with brine (100 mL). This solution containing the crude aminosulfonamide VII product (ca. 27.9 g) was used "as is" in the next step.

HPLC: 95:5 trans/cis (above method).

Step F: Maleate Salt Formation Procedure

The ethyl acetate solution containing aminosulfonamide VII (ca. 27.9 g, 86 mmol; 95:5 trans/cis) from step 5 was concentrated by distillation (1 atm) to a volume of 70 mL. Acetone (250 mL) was added and the concentration repeated to a volume of 70 mL. The operation was repeated, this time concentrating to a volume of 160 mL. Maleic acid (9.98 g, 86 mmol) was added. The mixture was stirred until the salt crystallized, and was then stirred for 12–18 h at 20°–22° C. The mixture was filtered, and the product cake washed with acetone (1 bed volume). The product was air-dried, then dried in vacuo (100 mBar, nitrogen sweep, 75° C.) to constant weight.

Yield: 33.0 g (92%) of the maleate salt VIII as a white crystalline solid. HPLC: 99:1 trans/cis (above method). $^1$H NMR: (DMSO-d$_6$) δ8.17 (br s, 2H), 7.81 (s, 1H), 6.05 (s, 2H), 4.61 (br s, 1H), 4.08–4.00 (m, 1H), 3.24–3.14 (m, 1H), 3.06–2.93 (m, 1H), 2.7–2.45 (m, 2H), 1.39 (d, 3H, J=6.7 Hz), 1.20 (t, 3H, J=7.1 Hz). Microanalysis: Anal. Calcd for C$_{14}$H$_{20}$N$_2$O$_4$S$_3$: C, 38.17; H, 4.58; N, 6.39; S, 21.83. Found: C, 38.19; H, 4.58; N, 6.29; S, 21.60.

Step G: Crude Hydrochloride Salt Formation Procedure

To a mechanically stirred mixture of ethyl acetate (250 mL) and saturated aqueous sodium bicarbonate (120 mL) was added maleate salt VIII (33.0 g, 75 mmol; 99:1 trans/cis). The mixture was stirred at 20°–25° C. until all of the solid dissolved, and the two phases became clear. The mixture was allowed to settle and the layers then separated. The aqueous (lower) phase was extracted with ethyl acetate (50 mL). The organic layers were combined and then washed with saturated aqueous sodium chloride (50 mL). To the well stirred ethyl acetate solution was slowly added concentrated hydrochloric acid (12M, 6.25 mL, 75 mmol). During the addition the product crystallized. The mixture was concentrated in vacuo (200 mBar, 45° C.), replacing the ethyl acetate as necessary, until the water content of the solution was less than 0.1 mg/mL at a volume of 150 mL. The mixture was cooled to 20°–22° C. and then stirred for 12–18 h at this temperature. The mixture was filtered, and the product cake washed with ethyl acetate (2×25 mL) The product was air-dried, then dried in vacuo (100 mBar, nitrogen sweep, 45°–50° C.) to constant weight.

Yield: 26.4 g (98% yield; 64% overall yield from hydroxysulfone II) of the crude aminosulfonamide hydrochloride salt I as a white crystalline solid. HPLC: >99% (above HPLC method).

Step H: Recrystallization Procedure

A mechanically stirred suspension of crude aminosulfonamide hydrochloride salt I (26.4 g, 73 mmol) in water (70 mL) was heated at 90°–95° C. until all of the solid dissolved. To the hot solution was added activated carbon (Darco KB, 0.26 g), and the mixture stirred for 15 min at 90°–95° C. The mixture was filtered hot (85°–90° C.) through a well-washed bed of filter aid (SuperCel). The filter cake was washed with boiling water (9 mL). The filtrate and cake wash were combined, and the product allowed to crystalize as well-stirred solution was cooled to 60° C. The mixture was stirred for 1 h at 60° C., or until the product had convened to the thermodynamically more stable hemihydrate crystal form. The mixture was then slowly cooled to 3° C., and then stirred for 1 h at this temperature. The mixture was filtered cold, using the mother liquors to rinse the cake. The product was air-dried, then dried in vacuo (100 mBar, nitrogen sweep, 45°–50° C.) to constant weight.

Yield: 24.2 g (92% yield; 59% overall yield from hydroxysulfone II) of pure aminosulfonamide hydrochloride salt I as a white crystalline solid. HPLC: 99.9 area % (254 nm), 99.6 wt % vs an external standard, >99% (4S,6S) as the N-TFA derivative. Specific Rotation: $[\alpha]_{589} = -17.1°$ (c=1.00, $H_2O$). MP: 238° C. dec. (DSC, 2° C./min ramp). $^1H$ NMR: (DMSO-$d_6$) δ9.91 (br s, 1H), 9.63 (br s, 1H), 8.21 (s, 2H), 8.02 (s, 1H), 4.68 (br s, 1H), 4.37 (m, 2H), 3.19 (br s, 1H), 3.04 (br s, 1H), 2.80 (d, 1H), 2.55 (m, 1H), 1.39 (d, 3H), 1.29 (d, 3H). $^{13}C$ NMR: (DMSO-$d_6$) δ149.7 (s), 141.9 (s), 137.4 (s), 130.7 (s), 51.6 (s), 49.2 (s), 40.8 (s), 30.7 (s), 11.1 (s), 10.0 (s). Microanalysis: Anal. Calcd for $C_{10}H_{17}N_2O_4S_3Cl$: C, 33.28; H, 4.75; N, 7.76; S, 26.66; Cl, 9.84. Found: C, 33.33; H, 4.70; N, 7.67; S, 26.60; Cl, 9.77.

What is claimed is:

1. A process for the preparation of a Compound of structural formula I:

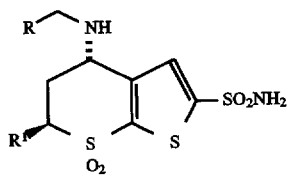

and its hydrochloride salt wherein chirality at C-6 is fixed, and the trans-stereochemical relationship between C-4 and C-6 substituents is retained, compound is crystalline and R and $R^1$ are the same or different and are $C_{1-3}$ alkyl, which comprises the steps of:

A) treating a compound of formula II with

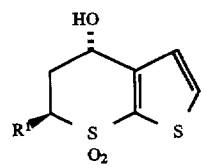

a nitrile of formula RCN and a strong acid, such that the amount of water present, depending on the acid employed, is from about 0.5 to about 10 wt %, to form a compound of Structure III:

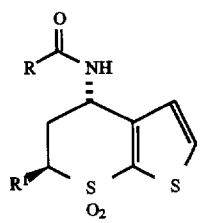

B) treating III with chlorosulfonic acid to form a compound of Structure IV:

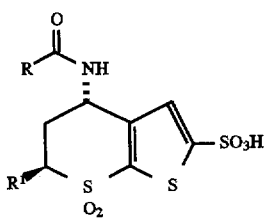

C) treating IV with thionyl chloride to form a compound of Structure V:

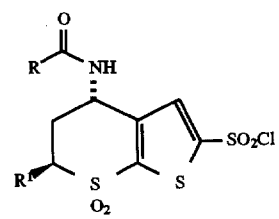

D) treating V with ammonia to form a compound Structure VI:

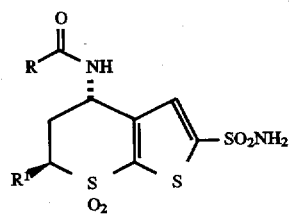

E) treating VI with sodium borohydride and a strong acid, or borane-tetrahydrofuran or borane-dimethyl sulfide to form a compound of Structure VII

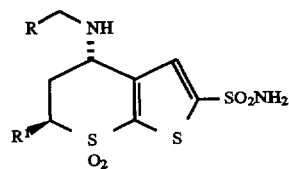

F) isolation of VII as the maleate salt VIII;

G) conversion of VIII to the hydro chloride salt of I; and

H) purification of the hydrochloride salt of I.

2. The process of claim 1, wherein R and $R^1$ are methyl.

3. The process of claim 1, wherein R is methyl and $R^1$ n-propyl.

4. A process for the preparation of a compound of structural formula III:

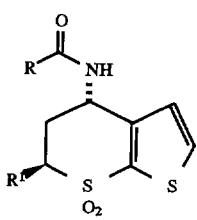

wherein chirality at C-6 is fixed, and the trans-stereochemical relationship between C-4 and C-6 substituents is retained and R and $R^1$ are the same or different and are $C_{1-3}$ alkyl, which comprises:

treating a compound of formula II with

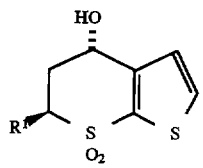

a nitrile of formula RCN and a strong mineral acid such that the amount of water present, depending on the acid employed, is from about 0.5 to about 10 wt %.

5. The process of claim 4, wherein R and $R^1$ are methyl.

6. The process of claim 4, wherein R is methyl and $R^1$ is n-propyl.

7. The process of claim 1 wherein the strong acid is concentrated sulfuric acid or a mixture of concentrated sulfuric acid and fuming sulfuric acid, methanesulfonic, trifluoroacetic acid, borotrifluoride etherate, or aluminum chloride and the mount of water present, is from about 1 to about 2 wt %.

8. The process of claim 1 wherein the Compound of structural formula I is crystallize by dissolving crude formula I in an aqueous solution at a temperature of about 90° C. to about 95° C., adding activating carbon, stirring the mixture, filtering the mixture through a bed of filter aid, washing the filter cake with a hot aqueous solution, combining the filtrate and cake, crystallizing formula I as the solution is cooled to about 1° C. to 5° C., filtering the mixture, collecting the cake and drying the cake.

* * * * *